United States Patent [19]

Nagano et al.

[11] Patent Number: 5,547,858
[45] Date of Patent: Aug. 20, 1996

[54] METHOD FOR PURIFICATION OF AMINO ACIDS, NUCLEIC ACIDS USING A HYDROCYCLONE

[75] Inventors: Yoshimi Nagano, Kawasaki; Takao Suganuma, Yokohama; Kazuhiro Satoh; Masao Ikeda, both of Kawasaki, all of Japan

[73] Assignee: Ajinomoto Co., Inc., Tokyo, Japan

[21] Appl. No.: 272,655

[22] Filed: Jul. 11, 1994

Related U.S. Application Data

[63] Continuation of Ser. No. 730,657, Jul. 16, 1991, abandoned.

[51] Int. Cl.$^6$ .............................. C07H 1/06; C07H 21/00; C07H 19/00; C12P 13/04
[52] U.S. Cl. .............................. 435/89; 435/87; 435/106; 536/26.73; 536/55.3
[58] Field of Search ................... 536/55.3, 26.73, 536/26.1, 55.3; 562/433; 127/58, 61, 62; 435/87, 89, 106

[56] References Cited

U.S. PATENT DOCUMENTS

| | | | |
|---|---|---|---|
| 1,708,940 | 4/1929 | Daly | 127/58 |
| 3,503,803 | 3/1970 | Bennett et al. | 127/58 |
| 3,883,365 | 5/1975 | Forsberg et al. | 127/60 |

FOREIGN PATENT DOCUMENTS

| | | |
|---|---|---|
| 3842751 | 7/1990 | Germany . |

OTHER PUBLICATIONS

Kirk–Othmer Encyclopedia of Chemical Technology, vol. 5, Third Edition, John Wiley & Sons, New York: 1979, pp. 226–227.

The DorrClone Hydrocyclone product Brochure, Dorr–Oliver, Bulletin DC–2, 1989.

*Primary Examiner*—Gary L. Kunz
*Attorney, Agent, or Firm*—Oblon, Spivak, McClelland, Spivak, & Neustadt, P.C.

[57] ABSTRACT

Crystals of an amino acid, a nucleic acid or a derivative thereof can be efficiently isolated and purified at low cost from a solution containing the crystals, bacterial cells and medium components by using a liquid cyclone.

18 Claims, 2 Drawing Sheets

METHOD FOR PURIFICATION OF AMINO ACIDS, NUCLEIC ACIDS USING A HYDROCYCLONE

This is a continuation of application Ser. No. 07/730,657, filed Jul. 16, 1991, now abandoned.

BACKGROUND OF THE INVENTION

1. Field of the Invention

The present invention relates to a method for efficiently isolating and purifying crystals, especially of amino acids, nucleic acids or derivatives thereof from solutions containing both crystals and bacterial cells.

2. Discussion of Background

As methods for separating crystals in a culture broth or an enzyme reaction solution, filtration or centrifugal precipitation has heretofore been used generally. Where cells are contained in the solution to be treated, however, the cells tend to cause clotting of the filter cloth during filtration and most of the cells are taken up into the crystals so that filtration is not suited for separation of crystals. Using centrifugal precipitation, represented by the decanter type, it is possible to isolate crystals but selection of cells and adhered mother liquor is insufficient. It is thus necessary to perform multiple step separations and additional countercurrent washing where loss in separation of crystals is unavoidable. In another method, an acid or a base is added to dissolve the crystals, and after removing the cells from the solution, recrystallization must be performed.

A liquid cyclone is well known as a wet type classifying machine which gives a centrifugal force in a fixed cylinder by rotating liquid and has been widely used for recovery of finely ground matter in a mine, removal of sand grains from pulp, classification of various starches, etc. These are all due to application of the function of a liquid cyclone to classify particles having a diameter larger than the critical diameter into the downstream side. In this case, however, a liquid cyclone fails to classify particles having a diameter smaller than the critical diameter and these particles are merely classified by a ratio of liquid volume at the upstream to that at the downstream. This concept is conventionally applied to a crystal slurry of a solution containing crystals to be concentrated using a liquid cyclone. But, when a solution containing cells is fed to the liquid cyclone, the cells have a diameter, smaller than the critical diameter so that there is no difference in concentration between the upstream and the downstream of the liquid cyclone, which makes separation of the cells impossible. Therefore, there is a need for a method to efficiently isolate crystals from a solution containing cells using fewer steps and at low cost.

SUMMARY OF THE INVENTION

As a result of extensive investigations to solve the foregoing problems, the present inventors have found that by applying a liquid cyclone to a solution containing both crystals and cells, the crystals can be efficiently concentrated and isolated by the ability of classification of the liquid cyclone and at the same time, the cells having a diameter smaller than that of the crystals, which are considered difficult to apply the liquid cyclone thereto, can be efficiently selected from a concentrated solution of the crystals.

Accordingly, one object of the invention is to provide a method for purification of an amino acid, a nucleic acid or a derivative thereof comprising treating a crystal slurry containing not greater than 10 wt % of cells having a diameter of not greater than 5 µm on a dry weight basis, and 5 to 60 wt % of crystals of an amino acid, a nucleic acid or derivatives thereof, having a diameter of 10 to 2000 µm, with a liquid cyclone which has a representative diameter capable of sufficiently increasing the concentration of the crystals at the downstream side and, if necessary, applying a back pressure to the downstream side to recover a concentrated solution of crystals having 30 to 90 wt % at the downstream side and select not less than 50% of the cells at the upstream side.

DETAILED DESCRIPTION OF THE PREFERRED EMBODIMENTS

Figure 1:
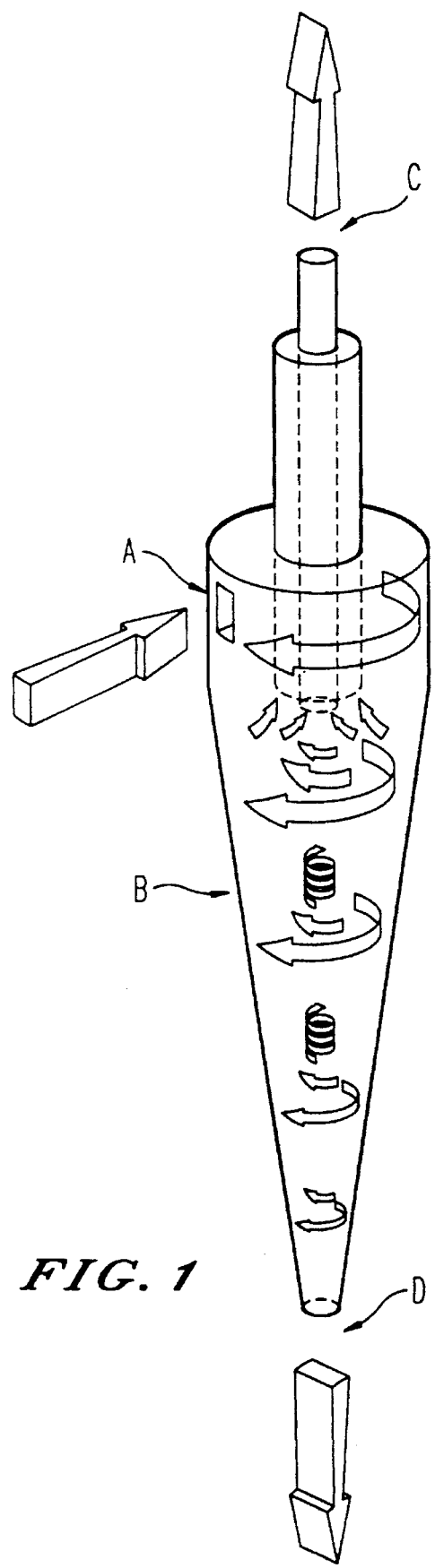
FIG. 1: A liquid cyclone.

The crystal slurry containing not greater than 10 wt % of cells having a diameter of not greater than 5 µm on a dry weight basis and 5 to 60 wt % of crystals of an amino acid, a nucleic acid or a derivative thereof having a diameter of 10 to 2000 µm is firstly fed to the liquid cyclone through a pump. The liquid cyclone used may be of conventional shape as shown in FIG. 1 and has a representative diameter small enough to sufficiently increase the crystal concentration at the downstream side. By selecting the feeding pressure, the crystals are transported to the downstream side due to a centrifugal effect inside the liquid cyclone, whereby the crystal concentration at the downstream side is increased. At the same time, the cells are less affected by the centrifugal effect of the liquid cyclone and conveyed mainly to the upstream side, because the concentration of the crystals concentrated at the downstream side becomes high, though the cells show a behavior similar to that of the solution. Therefore, the crystals and the cell solution can be efficiently separated from each other. Taking leakage of the crystals at the upstream side into account, a back pressure is also applied to the downstream side, if necessary, whereby the crystal concentration at the downstream side increases and selection of the cells is simultaneously accelerated.

As described above, the crystals can also be efficiently separated from a solution containing three components containing crystals, cells and medium ingredients using a liquid cyclone.

The thus obtained concentrated solution of crystals is filtered or dehydrated by centrifugation. Thus it is possible to isolate good crystals having a good selection of cells and less mother liquor adhered, as compared to conventional centrifugal precipitation. This result is obtained because in the concentrated solution of crystals obtained after treatment, the cells have been selectively removed and fine crystals, which also cause reduced velocity of filtration or dehydration as the cells do, are simultaneously selectively removed. Whereas the solution prior to treatment causes clotting of filter cloth due to the presence of the cells and is therefore not suitable for use.

Sources of crystal slurries to which the present invention is applied are slurries derived from culture solutions or enzyme reaction solutions of amino acids, nucleic acids or derivatives thereof in which the crystals are precipitated (e.g., guanosine fermentation solution), slurries containing crystals which are precipitated by adding an acid or a base thereto after fermentation or enzyme reaction is completed (e.g., glutamic acid fermentation solution), slurries containing crystals which are precipitated by concentrating or cooling after fermentation or enzyme reaction is completed (e.g., tryptophan fermentation solution). All these mixtures contain cells and crystals of an amino acid, a nucleic or a derivative thereof produced by the cells.

Examples of such crystal slurries include solutions containing various amino acids such as phenylalanine, leucine, isoleucine, glutamine, aspartic acid or derivatives thereof in addition to glutamic acid or tryptophan described above, and cells capable of producing them. The present invention also applies to crystal slurries of nucleosides, nucleotides or derivatives thereof, in addition to guanosine described above, which is obtained by fermentation or enzyme reaction.

Furthermore, the method of the present invention is much more efficient when combined with the step of fermentation or enzyme reaction. By withdrawing crystals of an amino acid, a nucleic acid or a derivative thereof produced by the fermentation or enzyme reaction from a tank as they are, the fermentation or enzyme reaction proceeds smoothly. At the same time procedures at the treatment step are simplified, whereby productivity of the amino acid, the nucleic acid or the derivative thereof are enhanced and production costs are reduced.

Figure 2:
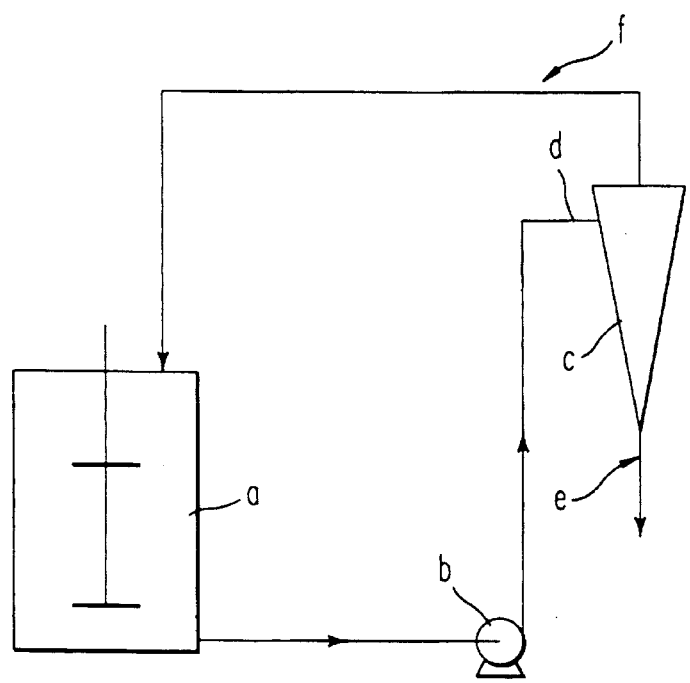
FIG. 2: An example of a fermentation tank or reaction tank connected with a liquid cyclone.

In order to isolate and recover crystals of the amino acid, the nucleic acid or the derivative thereof formed during the fermentation or enzyme reaction, the culture broth or reaction solution containing the crystals is withdrawn continuously or intermittently and the crystals are isolated using a liquid cyclone. An example of connecting a fermentation tank or reaction tank with the liquid cyclone is illustrated in FIG. 2. At the downstream side, a concentrated solution of the crystals is obtained. By purifying the crystals, the amino acid, the nucleic acid or derivatives thereof having higher purity are obtained.

The medium components and the cells are contained at the upstream side, which may be recycled to the fermentation tank or reaction tank to provide them again for the production.

In another method, since the upstream solution also contains the product which has not crystallized but is in a dissolved state, the amino acid, the nucleic acid or the derivative thereof may be collected from the solution in a conventional manner such as crystallization by concentration or by the resin method. Also where the fermentation or enzyme reaction is completed, the crystals can be isolated and collected from the culture broth or the reaction solution. The product which is in a dissolved state may also be collected in a conventional manner such as crystallization by concentration or by the resin method, singly or in combination.

According to the method of the present invention, the solution containing the crystals and cells is supplied to a liquid cyclone, whereby the crystals are conveyed at the downstream side by the centrifugal effect in the inside of the liquid cyclone and recovered as a concentrated solution of crystals, the cells are less affected by the centrifugal effect and show a behavior similar to that of the solution, but most of them are withdrawn at the upstream side because of an increased concentration of the crystals concentrated at the downstream side. Therefore, the crystals can be efficiently separated from the solution.

Separation and purification of the crystals using a liquid cyclone are advantageous from various aspects as compared to those using a conventional centrifugal machine, since facility investment is very inexpensive, maintenance is easy, the liquid cyclone is compact, has a large processing ability but does not require a large space, energy consumption is inexpensive because of using only a pump effort, procedures and operations are simple, multiple step processing and countercurrent washing are easy, etc.

Other features of the invention will become apparent in the course of the following descriptions of exemplary embodiments which are given for illustration of the invention and are not intended to be limiting thereof.

EXAMPLE 1

Figure 3:
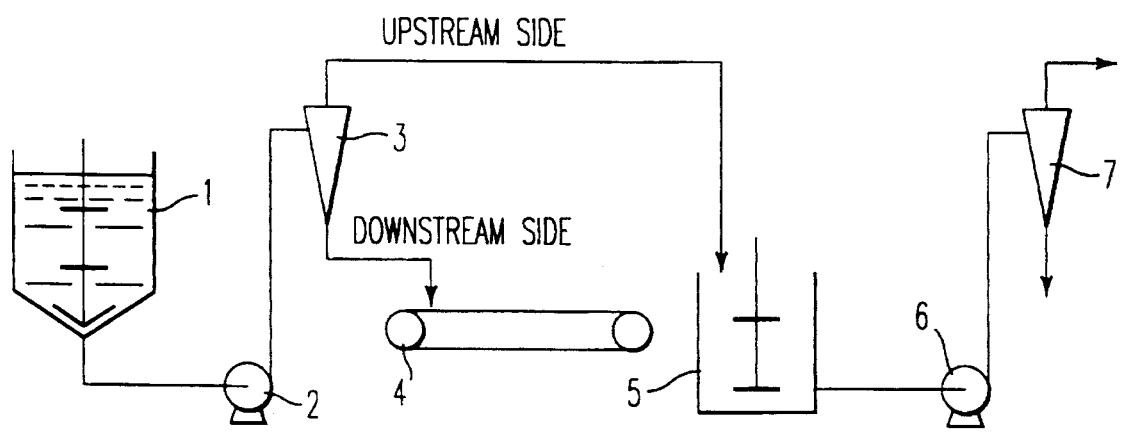
FIG. 3: An example of a process of separating and purifying crystals from a fermentation solution using liquid cyclones.

A glutamic acid fermentation solution containing 1 wt % of glutamic acid-producing bacterial cells, on a dry weight basis of the cells was charged, in a tank (1) for crystallization shown in FIG. 3. Sulfuric acid was added to the fermentation solution and neutralization crystallization was performed at pH 3.2. The slurry of glutamic acid crystals obtained by the crystallization contained 10 vol % of crystals and the diameter of the crystals was approximately 2 to 300 μm. The slurry containing glutamic acid crystals was fed into a liquid cyclone (3) via a pump (2). The liquid cyclone (3) has an ordinary shape as a cyclone, is made of ceramic and has a representative diameter of 20 mm at the cylinder portion. The feed pressure was set at 5 kg/m$^2$G and the feed volume per liquid cyclone was 0.72 m$^3$/Hr. A back pressure of 0.5 kg/m$^2$G was applied to the downstream port of the liquid cyclone but no back pressure was applied to the upstream port. By this operation, crystals of glutamic acid were obtained at the downstream side of the liquid cyclone, as a concentrated solution containing 90 wt % of the crystals, and more than 90% of the cells in the feed solution was selectively removed. The recovery rate of crystals at the downstream side of the liquid cyclone was 80%. Next, the concentrated solution of the crystals obtained was treated with a flat belt filter (4) of Pannevis. As the result, an average specific filtration resistance became 109 n/kg in a cake thickness of 30 mm, indicating that the filtering property was good. Further by using 0.5 kg of washing water per 1 kg of dry cake weight, the crystals of glutamic acid having 2.5% of the mother liquor adhered to the cake and 2% of the cell intake based on the feed solution were obtained.

The solution at the upstream side of the liquid cyclone (3) was stored in a stocker (5) and then fed into a liquid cyclone (7) via a pump (6). The liquid cyclone (7) has a shape similar to the liquid cyclone (3), is made of ceramic and has a representative diameter of 9 mm at the cylinder portion. The feed pressure was set at 5 kg/m$^2$G and the feed volume per liquid cyclone was 0.24 m$^3$/Hr. Back pressure was not applied either to the downstream port or to the upstream port of the liquid cyclone. The crystals which leaked into the upstream side of the liquid cyclone (3) were recovered at the downstream side and able to be recycled to the tank (1) for crystallization. The solution at the upstream side of the liquid cyclone (7) was sent to further processing for purification.

By designing the system as described above, the crystals of glutamic acid could be efficiently isolated and purified from the solution containing glutamic acid crystals and glutamic acid-producing bacterial cells.

EXAMPLE 2

Because of the very low solubility of guanosine, guanosine crystals are already precipitated in a guanosine fermentation solution having a concentration of 2.5 g/dl after completion of the fermentation steps. The particle diameter of guanosine crystals is approximately 2 to 200 μm. The fermentation solution of guanosine containing the guanosine-producing bacterial cells was fed into a liquid cyclone similar to the liquid cyclone (7) used in Example 1. Feed pressure was set at 5 kg/m²G and feed volume per liquid cyclone was 0.24 m³/Hr. Back pressure of 0.5 kg/m²G was applied to the downstream port of the liquid cyclone but no back pressure was applied to the upstream port. By this operation, 70% of guanosine crystals were recovered at the downstream side of the liquid cyclone, and 80% of the cells in the feed solution was selectively removed. By performing twice the so-called step of water washing, by adding about a 3-fold volume of water to the thus obtained concentrated solution of crystals and applying the mixture to the liquid cyclone, a concentrated solution of guanosine crystals having a cell selectivity increased to 99% or more was obtained at a recovery rate of 50%, from which impurities in the feed solution including coloring materials had further been sufficiently selectively removed. Since intake of impurities into the crystals precipitated during fermentation of guanosine is small, the concentrated solution obtained by this procedure had a purification degree sufficient to provide the product after the following separation and drying as it was. Further in performing multiple liquid cyclone procedures, a recovery rate of the crystals could be further increased by performing multiple countercurrent washing.

As described above, crystals of guanosine could be efficiently isolated and purified from a fermentation solution containing guanosine-producing bacterial cells and the guanosine crystals precipitated.

EXAMPLE 3

A tryptophan fermentation solution having a tryptophan concentration of 2 g/dl was cooled to 15° C. to induce crystallization. The particle diameter of the resulting tryptophan crystals was approximately 2 to 150 μm. The fermentation solution of tryptophan containing the tryptophan-producing bacterial cells was fed into a liquid cyclone similar to the liquid cyclone (7) used in Example 1. Feed pressure was set at 5 kg/m²G and feed volume per liquid cyclone was 0.24 m³/Hr. Back pressure of 1.0 kg/m²G was applied to the downstream port of the liquid cyclone but no back pressure was applied to the upstream port. By this operation, about 60% of tryptophan crystals were recovered at the downstream side of the liquid cyclone, and about 80% of the cells in the feed solution was selectively removed. By performing two steps of the same washing as in Example 2 to the thus obtained concentrated solution of crystals, a concentrated solution of tryptophan crystals having a cell selectivity increased to 99% or more, from which impurities in the feed solution including coloring materials had further been sufficiently selectively removed, was obtained in a recovery rate of 45%. Since intake of the impurities into the crystals precipitated by cooling the fermentation solution is as small as in guanosine crystals of Example 2, the concentrated solution obtained by the procedures had a purification degree sufficient to provide the product after separation and drying without further purification.

As described above, the crystals of tryptophan could be efficiently isolated and purified from a solution containing tryptophan crystals precipitated by cooling and tryptophan-producing bacterial cells.

EXAMPLE 4

Brevibacterium flavum AJ 3409 (FERM-BP 662) was inoculated on agar plate medium containing 1% yeast extract, 1% peptone, 0.5% sodium chloride and 0.5% glucose followed by culturing at 31° C. for 24 hours. In 30 Sakaguchi flasks, each having a 500 ml volume, were charged 25 ml each of medium (pH 7.0) composed of 4% glucose, 0.1% potassium phosphate, 0.04% magnesium sulfate, 0.001% iron sulfate, 0.2% ammonium sulfate, 0.4% urea, 4 μg/l biotin, 100 μg/l vitamin $B_1$ and 0.035% (calculated as total nitrogen) of soybean protein hydrolysate. After sterilization by heating at 121° C. for 15 minutes, the temperature was lowered to room temperature and one platinum loopful of the cells of Brevibacterium flavum AJ 3409 previously grown on the agar plate medium was inoculated on the sterilized medium. By shake culturing at 31° C. for 24 hours, a seed culture broth was prepared. In a fermentation tank of 20 liter volume, was charged 10 liters of medium (pH 7.0) composed of 10% glucose, 0.4% potassium phosphate, 0.06% magnesium sulfate, 0.002% iron sulfate, 5% ammonium sulfate, 8 μg/l biotin, 500 μg/l vitamin $B_1$ and 0.056% (calculated as total nitrogen) of soybean protein hydrolysate. After sterilization by heating at 121° C. for 20 minutes, the temperature was lowered to room temperature and the seed culture broth previously cultured in the flask was added to the medium followed by culturing under conditions: culture temperature at 30° C., controlled pH of 6.5, aeration amount of ½ vvm, a stirring number of 600 rpm and inner pressure of 0.2 kg/cm². Immediately before the glucose in the culture broth was consumed, a solution (sterilized) containing 45 g/l of glucose was added to the culture tank to replenish the glucose concentration in the culture broth and always maintain a concentration of 0.1 to 1.5%. At and from the time period when the amount of accumulated glutamine exceeded its solubility and the crystals of glutamine began to crystallize in the culture broth, a part of the culture broth was aseptically taken out of the system then passed through a small-sized liquid cyclone to isolate the crystals. Then the culture broth was returned to the culture tank. Culture for 100 hours by this method gave 1.1 kg (moisture content of 16.6%) of a slurry of glutamine crystals and 15 liters of the culture broth containing 5.2% glutamine. The obtained culture broth was crystallized by concentration. The crystals were isolated and combined with the slurry of crystals obtained during the culture. By repeating dissolution and crystallization three times, 1.36 kg of glutamine crystals was obtained in a high purity.

On the other hand, culture was carried out for 100 hours under the same conditions except that the culture broth was not recycled to the liquid cyclone and the crystals formed during the culture were not isolated. As the result, 14.4 liters of the culture broth containing 9.7% of glutamine was obtained. By repeating dissolution and crystallization of the crystals obtained by concentration and crystallization, glutamine was purified. However, it was necessary to repeat the dissolution and crystallization four times in order to obtain glutamine crystals having the same purity as those obtained in the method previously shown. As a result, 0.98 kg of glutamine crystals of high purity was obtained.

With respect to the two methods for preparing glutamine, the results and characteristics are shown in Table 1.

TABLE 1

|  | Culture with Isolation of Crystals (present invention) | Culture without Isolation of Crystals (prior art) |
| --- | --- | --- |
| Fermentation: | | |
| Productivity | 1.13 g/l · hr | 0.97 g/l · hr |
| Yield | 52% | 47% |
| Treatment: | | |
| Number of steps | 3 steps | 4 steps |
| Yield | 81% | 70% |

EXAMPLE 5

*Brevibacterium lactofermentum* ATCC 21420 was inoculated on agar plate medium containing 1% yeast extract, 1% peptone, 0.5% sodium chloride and 0.5% glucose followed by culturing at 31° C. for 24 hours. In 30 Sakaguchi flasks, each having a 500 ml volume, were charged 25 ml each of medium (pH 7.0) composed of 2% sucrose, 0.1% potassium phosphate, 0.04% magnesium sulfate, 0.001% iron sulfate, 0.001% manganese sulfate, 0.4% ammonium acetate, 0.04% tyrosine, 100 µg/l biotin, 100 µg/l vitamin $B_1$ and 0.2% (calculated as total nitrogen) of soybean protein hydrolyzate. After sterilization by heating at 121° C. for 15 minutes, the temperature was lowered to room temperature and one platinum loopful of the cells of *Brevibacterium lactofermentum* ATCC 21420 previously grown on the agar plate medium was inoculated on the sterilized medium. By shake culturing at 31° C. for 24 hours, a seed culture broth was prepared. In a fermentation tank of 20 liter volume was charged 10 liters of medium (pH 7.0) composed of 10% glucose, 0.15% potassium phosphate, 0.1% magnesium sulfate, 0.001% iron sulfate, 50 µg/l biotin, 2000 µg/l vitamin $B_1$ and 0.08% (calculated as total nitrogen) of soybean protein hydrolyzate. After sterilization by heating at 121° C. for 20 minutes, the temperature was lowered to room temperature and the seed culture broth previously cultured in the flask was added to the medium followed by culturing under conditions: culture temperature at 31° C., controlled pH of 7, aeration amount of 3 vvm, a stirring number of 400 rpm and inner pressure of 0.2 kg/cm². Immediately before the glucose in the culture broth was consumed, a solution (sterilized) containing 45 g/l of glucose was replenished to the culture tank to control the glucose concentration in the culture broth to always keep it between 1.0 to 2.5%. At and from the time period when the amount of accumulated phenylalanine reached its solubility, a small amount of seed crystals of phenylalanine was added to the culture broth in order to facilitate crystallization of phenylalanine, and a part of the culture broth was aseptically taken out of the system, passed through a small-sized liquid cyclone to isolate the crystals. Then the culture broth was returned to the culture tank. Culture for 80 hours by this method gave 0.21 kg (moisture content of 20%) of a slurry of phenylalanine crystals and 15 liters of the culture broth containing 2.8% phenylalanine. The obtained culture broth was crystallized by concentration. The crystals were isolated and combined with the slurry of crystals obtained during the culture. By repeating dissolution and crystallization three times, 0.41 kg of phenylalanine crystals was obtained in a high purity.

On the other hand, culture was carried out for 80 hours under the same conditions except that the culture broth was not recycled to the liquid cyclone and the crystals formed during the culture were not isolated. As the result, 15 liters of the culture broth containing 3.5% of phenylalanine was obtained. By repeating dissolution and crystallization of the crystals obtained by concentration and crystallization, phenylalanine was purified. However, it was necessary to repeat the dissolution and crystallization four times in order to obtain phenylalanine crystals having the same purity as those obtained in the method previously shown. As a result, 0.34 kg of phenylalanine crystals of high purity was obtained.

With respect to the two methods for preparing phenylalanine, the results and characteristics are shown in Table 2.

TABLE 2

|  | Culture with Isolation of Crystals (present invention) | Culture without Isolation of Crystals (prior art) |
| --- | --- | --- |
| Fermentation: | | |
| Productivity | 0.49 g/l · hr | 0.44 g/l · hr |
| Yield | 18.1% | 16.2% |
| Treatment: | | |
| Number of steps | 3 steps | 4 steps |
| Yield | 69.7% | 64.8% |

EXAMPLE 6

*Bacillus subtilis* AJ 11713 (FERM-BP 208) was inoculated on agar plate medium containing 3% soluble starch, 0.5% yeast extract and 0.5% peptone followed by culturing at 31° C. for 24 hours. In a small fermentation tank of 2 liter volume, was charged 1 liter of medium (pH 6.7) composed of 3% glucose, 0.1% potassium phosphate, 0.04% magnesium sulfate, 0.001% iron sulfate, 0.001% manganese sulfate, 0.3% ammonium sulfate, 0.5% sodium glutamate and 0.065% (calculated as total nitrogen) of soybean protein hydrolyzate. After sterilization by heating at 121° C. for 15 minutes, the temperature was lowered to room temperature and one platinum loopful of the cells of *Bacillus subtilis* AJ 11713 previously grown on the agar plate medium was inoculated on the sterilized medium. By shake culturing at 31° C. for 30 hours, a seed culture broth was prepared. In a fermentation tank of a 20 liter volume, was charged 10 liters of medium (pH 7.0) composed of 20% glucose, 0.2% potassium phosphate, 0.4% magnesium sulfate, 0.001% iron sulfate, 0.001% manganese sulfate and 0.05% (calculated as total nitrogen) of soybean protein hydrolyzate. After sterilization by heating at 121° C. for 20 minutes, the temperature was lowered to room temperature and the seed culture broth previously cultured in the small fermentation tank was added to the medium followed by culturing under conditions: culture temperature at 31° C., controlled pH of 6.7, aeration amount of ¾ vvm, a stirring number of 600 rpm and inner pressure of 0.2 kg/cm². Immediately before the glucose in the culture broth was consumed, a solution (sterilized) containing 45 g/l of glucose was replenished to the culture tank to control the glucose concentration in the culture broth to always keep it between 0.1 to 1.5%. At and from the time period when the amount of tryptophan accumulated exceeded its solubility and the crystals of tryptophan began to be crystallized in the culture broth, a detergent was added to the culture broth in order to facilitate crystallization of tryptophan, and a part of the culture broth was aseptically taken out of the system, passed through a small-sized liquid cyclone to isolate the crystals. Then the culture broth was returned to the culture tank. Culture for 100 hours by this method gave 0.28 kg (moisture content of 20%) of the slurry of tryptophan crystals and 13 liters of the culture broth containing 1.4% tryptophan. The obtained culture broth was crystallized by concentration. The crystals were isolated and combined with the slurry of the crystals obtained during the culture. By repeating dissolution and crystallization twice, 0.245 kg of tryptophan crystals was obtained in a high purity.

On the other hand, culture was carried out for 100 hours under the same conditions except that the culture broth was not recycled to the liquid cyclone and the crystals formed during the culture were not isolated. As the result, 13 liters of the culture broth containing 2.88% of tryptophan was obtained. By repeating dissolution and crystallization of the crystals obtained by concentration and crystallization, tryptophan was purified. However, it was necessary to repeat the dissolution and crystallization 3 times in order to obtain the tryptophan crystals having the same purity as those obtained in the method previously shown. As the result, 0.21 kg of tryptophan crystals of high purity was obtained.

With respect to the two methods for preparing tryptophane, the results and characteristics are shown in Table 3.

TABLE 3

|  | Culture with Isolation of Crystals (present invention) | Culture without Isolation of Crystals (prior art) |
| --- | --- | --- |
| Fermentation: |  |  |
| Productivity | 0.31 g/l · hr | 0.29 g/l · hr |
| Yield | 12% | 11% |
| Treatment: |  |  |
| Number of steps | 2 steps | 3 steps |
| Yield | 60% | 55% |

EXAMPLE 7

*Brevibacterium flavum* AJ 3686 (FERM-BP 755) was inoculated on agar plate medium containing 1% yeast extract, 1% peptone, 0.5% sodium chloride and 0.5% glucose followed by culturing at 31° C. for 24 hours. In 30 Sakaguchi flasks, each having a 500 ml volume, were charged 25 ml each of medium (pH 7.0) composed of 3% glucose, 0.1% potassium phosphate, 0.04% magnesium sulfate, 0.001% iron sulfate, 0.001% manganese sulfate, 0.3% urea, 10 μg/l biotin, 200 μg/l vitamin $B_1$ and 0.085% (calculated as total nitrogen) of soybean protein hydrolyzate. After sterilization by heating at 121° C. for 15 minutes, the temperature was lowered to room temperature and one platinum loopful of the cells of *Brevibacterium flavum* AJ 3686 previously grown on the agar plate medium was inoculated on the sterilized medium. By shake culturing at 31° C. for 24 hours, a seed culture broth was prepared. In a fermentation tank of 20 liter volume, was charged 10 liters of medium (pH 7.0) composed of 15% glucose, 0.1% potassium phosphate, 0.04% magnesium sulfate, 0.001% iron sulfate, 1% ammonium sulfate, 50 μg/l biotin, 300 μg/l vitamin $B_1$ and 0.01% (calculated as isoleucine) of soybean protein hydrolyzate. After sterilization by heating at 121° C. for 20 minutes, the temperature was lowered to room temperature and the seed culture broth previously cultured in the flask was added to the medium followed by culturing under conditions: culture temperature at 31° C., controlled pH of 7, aeration amount of ½ vvm, a stirring number of 600 rpm and inner pressure of 0.2 $kg/cm^2$. Immediately before the glucose in the culture broth was consumed, a solution (sterilized) containing 45 g/l of glucose was replenished to the culture tank to control the glucose concentration in the culture broth to always keep it between 0.1 to 1.5%. At and from the time period when the amount of leucine accumulated exceeded its solubility and the crystals of leucine began to crystallize in the culture broth, a part of the culture broth was aseptically taken out of the system, passed through a small-sized liquid cyclone to isolate the crystals. Then the culture broth was returned to the culture tank. Culture for 60 hours by this method gave 0.24 kg (moisture content of 16.6%) of the slurry of leucine crystals and 14 liters of the culture broth containing 2.6% leucine. The obtained culture broth was crystallized by concentration. The crystals were isolated and combined with the slurry of crystals obtained during the culture. By repeating dissolution and crystallization three times, 0.42 kg of leucine crystals was obtained in a high purity.

On the other hand, culture was carried out for 60 hours under the same conditions except that the culture broth was not recycled to the liquid cyclone and the crystals formed during the culture were not isolated. As the result, 13.7 liters of the culture broth containing 3.3% of leucine was obtained. By repeating dissolution and crystallization of the crystals obtained by concentration and crystallization, leucine was purified. However, it was necessary to repeat the dissolution and crystallization four times in order to obtain the leucine crystals having the same purity as those obtained in the method previously shown. As the result, 0.29 kg of leucine crystals of high purity was obtained.

With respect to the two methods for preparing leucine, the results and characteristics are shown in Table 4.

TABLE 4

|  | Culture with Isolation of Crystals (present invention) | Culture without Isolation of Crystals (prior art) |
| --- | --- | --- |
| Fermentation: |  |  |
| Productivity | 0.67 g/l · hr | 0.55 g/l · hr |
| Yield | 17% | 14.3% |
| Treatment: |  |  |
| Number of steps | 3 steps | 4 steps |
| Yield | 75% | 65% |

EXAMPLE 8

*Bacillus Subtilis* AJ 11312 (FERM-P 4823) was inoculated on agar plate medium containing 3% soluble starch, 0.5% yeast extract and 0.5% peptone followed by culturing at 34° C. for 24 hours. In a small fermentation tank of 2 liter volume, was charged 1 liter of medium (pH 6.4) composed of 3% glucose, 0.3% ammonium chloride, 0.1% potassium phosphate, 0.04% magnesium sulfate, 0.001% manganese sulfate, 0.05% yeast extract, 0.5% RNA and 0.12% (calculated as total nitrogen) of soybean protein hydrolyzate. After sterilization by heating at 121° C. for 15 minutes, the temperature was lowered to room temperature and one platinum loopful of the cells of *Bacillus subtilis* AJ 11312 previously grown on the agar plate medium was inoculated on the sterilized medium. By shake culturing at 34° C. for 30 hours, a seed culture broth was prepared. In a fermentation tank of 20 liter volume, was charged 10 liters of medium (pH 6.5) composed of 20% glucose, 0.2% potassium phosphate, 0.15% magnesium sulfate, 0.001% iron sulfate, 0.001% manganese sulfate, 0.13% (calculated as total nitrogen) of soybean protein hydrolyzate and 0.5% ammonium chloride. After sterilization by heating at 121° C. for 20 minutes, the temperature was lowered to room temperature and the seed culture broth previously cultured in the small fermentation tank was added to the medium followed by culturing under conditions: culture temperature at 35° C., controlled pH of 6.4, aeration amount of ½ vvm, a stirring number of 600 rpm and inner pressure of 0.2 kg/cm². Immediately before the glucose in the culture broth was consumed, a solution (sterilized) containing 45 g/l of glucose was replenished to the culture tank to control the glucose concentration in the culture broth to always keep it between 0.1 to 1.5%. At and from the time period when the amount of guanosine accumulated exceeded its solubility and the crystals of guanosine began to crystallize in the culture broth, a part of the culture broth was aseptically taken out of the system, passed through a small-sized liquid cyclone to isolate the crystals. Then the culture broth was returned to the culture tank. Culture for 100 hours by this method gave 0.65 kg (moisture content of 20%) of the slurry of guanosine crystals and 13.5 liters of the culture broth containing 0.4% guanosine. The obtained culture broth was crystallized by concentration. The crystals were isolated and combined with the slurry of crystals obtained during the culture. By repeating dissolution and crystallization twice, 0.43 kg of guanosine crystals was obtained in high purity.

On the other hand, culture was carried out for 100 hours under the same conditions except that the culture broth was not recycled to the liquid cyclone and the crystals formed during the culture were not isolated. As the result, 12.5 liters of the culture broth containing 3.5% of guanosine was obtained. By repeating dissolution and crystallization of the crystals obtained by concentration and crystallization, guanosine was purified. However, it was necessary to repeat the dissolution and crystallization three times in order to obtain the guanosine crystals having the same purity as those obtained in the method previously shown. As a result, 0.28 kg of guanosine crystals of high purity was obtained.

With respect to the two methods for preparing guanosine, the results and characteristics are shown in Table 5.

TABLE 5

|  | Culture with Isolation of Crystals (present invention) | Culture without Isolation of Crystals (prior art) |
| --- | --- | --- |
| Fermentation: |  |  |
| Productivity | 0.42 g/l · hr | 0.35 g/l · hr |
| Yield | 16% | 14% |
| Treatment: |  |  |
| Number of steps | 2 steps | 3 steps |
| Yield | 75% | 65% |

EXAMPLE 9

Pseudomonas sp. ATCC 19121 was inoculated on agar plate medium containing 1% meat extract, 1% peptone and 0.5% sodium chloride followed by culturing at 30° C. for 24 hours. In a small fermentation tank of 1 liter volume, was charged 0.3 liter of medium (pH 7) composed of 0.5% oleic acid, 0.5% soybean oil, 0.1% potassium phosphate, 0.1% magnesium sulfate, and 0.1% (calculated as total nitrogen) of soybean protein hydrolyzate. After sterilization by heating at 121° C. for 15 minutes, the temperature was lowered to room temperature and one platinum loopful of the cells of Pseudomonas sp. ATCC 19121 previously grown on the agar plate medium was inoculated on the sterilized medium. By shake culturing at 31° C. for 20 hours, a seed culture broth was prepared. In a fermentation tank of a 10 liter volume, was charged 5 liters of medium (pH 7) composed of 0.5% fumaric acid, 0.5% oleic acid, 0.5% soybean oil, 0.1% potassium phosphate, 0.1% magnesium sulfate 0.13% (calculated as total nitrogen) of soybean protein hydrolyzate. After sterilization by heating at 121° C. for 20 minutes, the temperature was lowered to room temperature and the seed culture broth previously cultured in the small fermentation tank was added to the medium followed by culturing under conditions: culture temperature at 31° C., aeration amount of ½ vvm, a stirring number of 600 rpm and inner pressure of 0.2 kg/cm². Twenty hours after the initiation of the culture, 1.5 kg of aspartic acid powders were sequentially replenished. While maintaining the pH at 5, the culture temperature was kept at 40° C. At and from the time period when the amount of alanine accumulated exceeded its solubility and the crystals of alanine began to crystallize in the culture broth, a part of the culture broth was aseptically taken out of the system, passed through a small-sized liquid cyclone to isolate the crystals. Then the culture broth was returned to the culture tank. Culture for 35 hours in total including the initial 20 hours by this method gave 6.3 kg (moisture content of 20%) of the slurry of alanine crystals and 5 liters of the culture broth containing 18% alanine. The obtained culture broth was crystallized by concentration. The crystals were isolated and combined with the slurry of the crystals obtained during the culture., By repeating dissolution and crystallization twice, 1.2 kg of alanine crystals was obtained in high purity.

On the other hand, culture was carried out for 35 hours under the same conditions except that the culture broth was not recycled to the liquid cyclone and the crystals formed during the culture were not isolated. As a result, 5 liters of the culture broth containing 28% of alanine was obtained. By repeating dissolution and crystallization of the crystals obtained by concentration and crystallization, alanine was purified. However, it was necessary to repeat the dissolution and crystallization 3 times in order to obtain the alanine crystals having the same purity as those obtained in the method previously shown. As a result, 1.1 kg of alanine crystals of high purity was obtained.

With respect to the two methods for preparing alanine, the results and characteristics are shown in Table 6.

TABLE 6

|  | Culture with Isolation of Crystals (present invention) | Culture without Isolation of Crystals (prior art) |
| --- | --- | --- |
| Fermentation: |  |  |
| Productivity | 8.2 g/l · hr | 8.0 g/l · hr |
| Yield | 93% | 89% |
| Treatment: |  |  |
| Number of steps | 2 steps | 3 steps |
| Yield | 87% | 80% |

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by

Letters Patent of the United States is:

1. A method for producing an amino acid, a nucleoside or a nucleotide thereof by fermentation, comprising the steps of:

culturing cells in a suitable culture medium sufficiently to produce a slurry containing cells and crystals of an amino acid, a nucleic acid or a derivative thereof, said cells having a diameter of not greater than 5 µm and being present in an amount not greater than 10 wt. % of said slurry on a dry weight basis, and said crystals having a diameter of 10 to 2000 µm and being present in an amount of 5 to 60 wt. % of said slurry, withdrawing said slurry, isolating said crystals with a liquid cyclone, said liquid cyclone having a diameter which sufficiently increases the concentration of crystals at the downstream side of said cyclone to recover a concentrated solution of crystals having a concentration of 30 to 90 wt. % at the downstream side and which selects not less than 80% of the cells at the upstream side, and recycling said cells at the upstream side of said cyclone to said culture medium.

2. The method of claim 1, wherein the concentrated solution of crystals at the downstream side is 60 to 80 wt. %.

3. The method of claim 1, wherein said slurry is derived from a culture broth and crystals are crystallized by adding an acid or a base after fermentation is complete.

4. The method of claim 1, wherein said slurry is derived from a culture broth and crystals are formed by concentration or cooling, after fermentation is complete.

5. The method of claim 1, further comprising applying a back pressure to the downstream side of said cyclone.

6. The method of claim 1, further comprising applying a back pressure of from 0 to 1.0 kg/m²G to the downstream side of said cyclone.

7. The method of claim 1, wherein said liquid cyclone has a cylinder portion, and said representative diameter of said liquid cyclone is about 20 mm at said cylinder portion.

8. The method of claim 1, wherein said amino acid, said nucleoside or said nucleotide is selected from the group consisting of guanosine, glutamic acid, tryptophan, phenylalanine, leucine, isoleucine, glutamine and aspartic acid.

9. The method of claim 1, wherein said isolating step selects not less than 90% of cells at the upstream side.

10. A method for purifying an amino acid, a nucleoside acid or a nucleotide, comprising the steps of:

sufficiently fermenting or culturing cells which produce said amino acid, said nucleic acid or said derivative thereof to form a slurry containing cells and crystals of said amino acid, said nucleic acid or said derivative thereof, said cells having a diameter of not greater than 5 µm and being present in an amount not greater than 10 wt. % on a dry weight basis, and said cells having a diameter of 10 to 2000 µm and being present in an amount of 5 to 60 wt. %;

separating at least some of said cells from at least some of said crystals with a liquid cyclone having a diameter sufficient to increase the concentration of crystals at the downstream side of said cyclone; and recovering a solution of crystals having a concentration of 30 to 90 wt. % at the downstream side of said cyclone and select not less than 80% of the cells at the upstream side of said cyclone.

11. The method of claim 10, further comprising, after said recovering step, the step of filtering or centrifuging the recovered concentrated solution of cells, thereby obtaining crystals with less adherence of mother liquor thereto.

12. The method of claim 10, wherein said separating and recovering steps select not less than 90% of the cells at the upstream side.

13. The method of claim 10, wherein said slurry is derived from a culture broth and crystals are crystallized by adding an acid or a base after fermentation is complete.

14. The method of claim 10, wherein said slurry is derived from a culture broth and crystals are formed by concentrating or cooling after fermentation is complete.

15. The method of claim 10, further comprising applying a back pressure to the downstream side of said cyclone.

16. The method of claim 10, further comprising applying a back pressure of from 0 to 1.0 kg/m²G to the downstream side of said cyclone.

17. The method of claim 10 wherein said liquid cyclone has a cylinder portion, and said representative diameter of said liquid cyclone is about 20 mm at said cylinder portion..

18. The method of claim 10 wherein said amino acid, said nucleoside or nucleotide is selected from the group consisting of guanosine, glutamic acid, tryptophan, phenylalanine, leucine, isoleucine, glutamine and aspartic acid.

* * * * *